(12) United States Patent
Nelson

(10) Patent No.: US 6,913,757 B1
(45) Date of Patent: Jul. 5, 2005

(54) **LIVE, AVIRULENT STRAIN OF *V. ANGUILLARUM* THAT PROTECTS FISH AGAINST INFECTION BY VIRULENT *V. ANGUILLARUM* AND METHOD OF MAKING THE SAME**

(75) Inventor: David R. Nelson, Wakefield, RI (US)

(73) Assignee: The Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 0 days.

(21) Appl. No.: 10/780,347

(22) Filed: Feb. 17, 2004

Related U.S. Application Data

(63) Continuation of application No. 09/915,706, filed on Jul. 26, 2001, now abandoned.
(60) Provisional application No. 60/220,733, filed on Jul. 26, 2000.

(51) Int. Cl.[7] .............................................. A61K 39/106
(52) U.S. Cl. ................................ 424/261.1; 424/200.1; 424/190.1; 435/243; 435/252.1; 435/252.3; 435/172.1
(58) Field of Search ........................... 424/261.1, 200.1, 424/190.1; 435/243, 252.1, 252.3, 172.1

(56) References Cited

U.S. PATENT DOCUMENTS 5,284,653 A * 2/1994 Wolf-Watz et al. ...... 435/252.1

\* cited by examiner

*Primary Examiner*—Jennifer E. Graser
(74) *Attorney, Agent, or Firm*—Gauthier & Connors LLP

(57) ABSTRACT

The present invention comprises the identification, characterization and sequencing of a gene within the *V. anguillarum* genome, the mugA gene, a live, attenuated strain of *V. anguillarum* which comprises a mutated mugA gene, methods of making the strain, vaccines comprising the strain and methods of making such vaccines and administering the vaccines to animals. The invention further comprises vaccines comprised of proteins encoded by the mugA gene, to methods of making such vaccines and administering the vaccines to animals, to vectors comprised of the attenuated strain of *V.anguillarum* and additional immunizing materials, methods of making the vectors and methods of administering the vectors to animals. Also disclosed are probes, passive vaccines and monoclonal antibodies for the detection and prevention of vibriosis.

20 Claims, 3 Drawing Sheets

```
   1 GTCGACTTAT TGCATTGATG GCGTACATGG TAGTGCCATC CTTCGTTTGC TAACAAGCGT TGTATAAAAG
  71 CTTGGTCGGT TTCATCAAGT TGAACACAAT ACTCATGATT TTTCCCACTT CCGGAAAGGG AAAAGTGAAA
 141 ATAGCTTTTG AGATCAGCCT GTTCTAGCAG CTTTTCAATG ATCTTTTTCG TCGTTACGTT TTGAAAAATC
 211 TGACCACTGC GTTTGTATTG CAACAAGCTA AGTGGATCCA ATATCTCTAT TTGATAATAA AACTGCTGCT
 281 TGTCTTTGCT ATATCCTGTG AATTGCAGAG TGCTACATAT ACCTGAAAAA AAACGCTTTC CAGAATCTAA
 351 TTCGTAAGAC ACACAAACAG CTTTACCTAG GTTTTTGGTA TCGATCTCCA TGTTTGCCGC GATGGAAACG
 421 GAAAACTGAC ACCCGCCGGA TACGCTTTCC TCTCCGATTA ATTGCGTGAC AATATAACTT TTGCTATCTG
 491 AAAGCTTAAT GGTGAGGGAG CGGGTTTGGT GCTTTAATTC GTTACTGCTC ATATTCAATT AATTCACTAT
 561 TAAATAAACA GTTCTAAAAG GCTGTTTATT GGATGAATAT TCGAAATTAT CACATAATAA TTCATGCTAT
 631 TATTACTTGC TGTATTGGTA TCAACTTTCA TGCTCTATAC ATGTAATATA TTTCGAGTTA GACCTTAATT
 701 CAACGTAATT TGTCTATTTA ATTATTATCT GAATAATATG TAATCGATTG CTTTGTGGTT ATTTTTATGT
 771 TTGTTTCATT TTTAATGACG GTGAGCTTGT GCATTCATAT TTTTTATGAT GACAACATCT TTGATGAAGT
 841 ATTTAAGATA TTGTTAATGC ATGAGGGGTT TGCGTGTATT TTTTATATTA AATCATAATA AAATCAACAA
 911 TATATGTTAT TTTGTGTCTT TTTATAGTGT TCTTTTAAAG AGGTAGGATG ACCTAAAGGT CGCCTAAATA
 981 TGGCGTAAAT TGCCATTGCT ATAATTCACC TCAAAGATAC ACTATTGGCA AATTGACAAA TATGTCACTT
1051 CGTATGAAAC AATATTAGTA GATGTTGTTT TTGCTGCAAA AATAAAAATT TTTCTGGTTG AAATAACTCA
1121 AGGCCTCTAG CGTTTTCCTT TATCTTAAAA TACAGGAAAT AGCGATTGAA GTTAATTGAC ACTTAAGCAA
         S-D         →ORF A/nupA
1191 ATACTCAACC TAACAGACCA GGAACCTATG CCTTTGTCAA AGCATCAAAT TGAGCAACTT TCTAAACCTC
1261 TGACTGATGA TTCGATCTGT GGCGTTTATC TTAAACTGGA AAAAAGTGCT TTTCGCCCAT TACGTAATGA
                                                     ↓
1331 ATTTAATGTC GCGCAAACTG CGCTGCGTAA GCTAAGTCAA AACCCTAGTG CTGACGAGAG AGATGCGTTA
1401 CAAGAGGCA TGTCTAAATA AGTGGAAGAT TCTCTCTGAC AGTTTGTACG AACAGTTTTC AAAAACAACC
1471 AGAGATATCG AGCTCATCTC ATGGTTTGTT GCTGCTCAAT TCCTTCTCGA TACCACATTA GAAAGTCCTG
1541 CGAATAGCCT TGAGTCGTTA GCGGATTTAA GTGAGAAGCA CTGGGATCAC CTCAACCCTG TACTACCAGT
1611 TGAAACGCTC AAATCTGATG ATGATAACGG CAAAGAAAGA GAGCAAGCAG ATGCGAAAGT TAAAGCATTT
1681 TTCCAACTAG TCGGCGATAG CGAGGAAAGC TCGATTCTCT ATGCGCCGGT GCTGCAACTG CCCTTAGTCG
1751 GGGAAGTGAC GTTTTTTGAC TTTCAAAGTG CAGAGAGAAA AGGCGAAATC AGCCAACTGA AATCTATGCT
1821 TACGACCACG GTGCCGCAAG AGCGTTTCGC AATTCAATTC AAGATGGAAA ACGCCAAACC TTGTGTCACC
1891 CAATTAGATC GTTTGTCAGC GTTGGTGAGC ACTAAGTGTC ATTCTCTAGG CAGTCAAAGT ACCAACTTCG
1951 GATTTGCGAA GTCACTGCTT ACCCGTGTTG AAAACGCTTT GGTTCATCTA AGTGGAATTA AGTTAGCACC
2031 GAAAGCGGAG GCCAAGACAG TAGAGCAAGA GGTTGCCGAA AGTTCAGTTT CTGAAGGGGA
     GCTGCCAAGC
2101 CATATGGATA CAAAACATAT AGAGCGAATA CCGATGGCAT CAGAGCAGGC TCAGACCGTA AGCCAACACT
2171 TACACGCAGG AAACCTCTCT GAACTGGGTA ATTTAAACAA TATGAACCGA GACTTAGCTT TCCATTTGTT
2241 GACAGAAGTC TCTGATTATT TTCGCCAGAG CGAACCGCAT AGCCCAATTT CATTTTTGTT AGAAAAAGCG
2311 ATTGCGATGG GATATTTATC CTTACCTGAG TTGCTGCGAG AAATGATGTC GGAACAAAAC GGTGACGCTC
2381 TTAGTACGAT TTTTAATGCC GCCGGATTGA ATCATCTCGA TCAGGTTTTG CTGCCGGAGG TGAGTACTCC
2451 AACGGTGGGC ATTGAAAAGCC CCCAAACACC TCAAGCGAAG CCTTCCGTTT CGGATCCCCG AAGTGTTGAA
2521 GAGCATGTAT CTCAGACTTC CCCTGTAGAT ACCCAATCTA AGCAAGATCA AAAACCACAA TCATCCGCTA
                                                    S-D         →ORF 3
2591 CGTCGGCTCT GAGTTGGTAA TTGTGTTTAA AAAATAAGGA AAAATCATGG CAAGTATTTA CATGCGTGTA
2661 AGCGGTCTTC AAGTTGAGGG CGCAGCGGACT ATCGGTCAGC TAGAAACGGC TGAAGGTAAA AATGACGGTT
2731 GGTTGCAAT CAACTCTTAC TCTTGGGGTG GCGCTCGTAA CGTTGCTATG GACATCGGTA ACGGCACCAA
2801 TGCGGATTCA GGCATGGTTG GCGTAAGCGA AGTTAGCGTA ACTAAAGAAG TCGATGGTGC TTCTGAAGAC
2871 CTACTGTCTT ATTTATTCAA CCCAGGTAAA GACGGTAAAA CTGTTGAGGT TGCATTTACT AAGCCTTCTA
2941 ACGATGGTCA AGGTGCAGAC GTTTACTTCC AAGTTAAGCT AGAAAAAGCA CGTTTAGTTT CTTACAACGT
3011 GAGCCGGACT GACGGATCTC AACCGTACGA GACCCTATCT CTTTCTTACA CTTCTATTTC TCAGAAGCAT
3081 CACTATGAGA AAGAAGGTGG TGAACTACAA AGCGGTGGTG TTGTGACTTA CGACCTACCG ACCGGGAAAA
3151 TGACTTCTGG TAAGTAATTC TTTCATTAGA CATGCCACGT TAATTGGCAT GTCTATTTCA TGAATATCTC
        S-D            →ORF C
3221 ATTTTAGGAC ACCGTTATGG CATTGAACTC ACAACATAAG CCCGTTAGTA AGAACCGTGT CAGCATCAC
3291 CTATGACGTT GAAACGAATG GCGCCGTAAA GACGAAAGAG CTGCCGTTTG TTGTTGGCGT CATTGGCGAC
3361 TTTTCAGGAC ACAAACCAGA ATCAGAAAAA GTTGATTTAG AAGAGCGAGA GTTCACGGGT ATCGATAAAG
3431 ACAACTTCGA TACAGTGATG GGGCAAATTC ACCCGCGTCT TTCGTACAAG GTTGATAACA AGCTTGCTAA
3501 TGATGATAGC CAGTTTGAAG TGAACTTGAG CCTCCGTTCG ATGAAAGATT TCCACCCAGA GAACTTAGTT
3571 GATNAAATTG AGCCGCTTAA
```

FIG. 2

1   MPLSKHQIEQLSKPLSDDSICGVYLKLEKSAFRPLRNEFNVAQTALRKLSQNPSADERDALQEACLNKWK
71  ILSDSLYEQFSKTTRDIELISWFVAAQFLLDTTLESAANSLEWLADLSEKHWDHLNPVLPVETLKSDDDK
141 GKEREQADAKVKAFFQLVGDSEESSILYAPVLQLPLVGEVTFFDFQSAERKGEISQLKSMLTTTVAQER
211 FAIQFKMENAKRCVTQLDRLSALVSTKCHSLGSQSTNFGFAKSLLTRVENALVHLSGIKLAPKAEAKTVE
281 QEVAESSVSEGELPSHMDTKHIERIPMASEQAQTVSQHLHAGNLSELGNLNNMNRDLAFHLLREVSDYFR
351 QSEPHSPISFLLEKAIRWGYLSLPELLREMMSEQNGDALSTIFNAAGLNHLDQVLLPEVSTPTVGIESPQ
421 TPQAKPSVSDPRSVEEHVSQTSPVDTQSKQDQKPQSSATSALSW*

FIG. 3a

1   MASIYMRVSGLQVEGAATIGQLETAEGKNDGWFAINSYSWGGARNVAMDIGNGTNADSGMVGVSEVSVTK
71  EVDGASEDLLSYLFNPGKDGKTVEVAFTKPSNDGQGADVYFQVKLEKARLVSYNVSGTDGSQPYESLSLS
141 YTSISQKHHY EKEGGELQSGGVVTYDLPTGKMTSGK*

FIG. 3b

1   MALNSQHKRVSKNRVSITYDVETNGAVKTKELPFVVGVIGDFSGHKPESEKVDLEEREFTGIDKDNFDTV
71  MGQIHPRLSYKVDNKLANDDSQFEVNLSLRSMKDFHPENLVDXIEPL

FIG. 3c

LIVE, AVIRULENT STRAIN OF V. ANGUILLARUM THAT PROTECTS FISH AGAINST INFECTION BY VIRULENT V. ANGUILLARUM AND METHOD OF MAKING THE SAME

CROSS-REFERENCE TO RELATED APPLICATIONS

This is a continuation of application Ser. No. 09/915,706, filed Jul. 26, 2001, now abandoned, which claims the benefit of U.S. Provisional Application No. 60/220,733, filed Jul. 26, 2000.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. 97352044811 awarded by the USDA.

BACKGROUND OF THE INVENTION

1. Field of the Invention

The present invention relates to the identification, characterization and sequencing of a gene, the mugA gene, and to a live, attenuated strain of V. anguillarum used as a vaccine against vibriosis.

2. Description on of the Related Art

Vibriosis is one of the major bacterial diseases affecting fish, bivalves and crustaceans in the marine environment. Vibrio anguillarum, a gram negative curved rod, is the causative agent of vibriosis. Symptoms of the disease in salmonids include red necrotic lesions in the abdominal muscle, erythema at the base of the fins, and subdermal hemorrhaging. The rectum becomes distended and filled with fluid, and hemorrhaging can often be observed in the internal organs. The bacteria become dispersed throughout the host tissues, including the kidney, liver and spleen. The highest concentration of bacteria is often found in the blood. Vibriosis typically culminates in a hemorrhagic septicemia that causes infected stocks to suffer mortalities ranging from 30–100%. As a result, vibriosis is a significant limitation to aquaculture, causing large economic losses to the industry.

The fish gastrointestinal tract has been implicated as a site of colonization and growth of pathogenic Vibrio species. (Home et al.; J. Fish Dis. 6: 461–471 (1983). It has been discovered that Vibrio ordalii and Vibrio anguillarum primarily infect the intestinal tracts and pyloric cecae of Pacific salmon. (Ransom et al.; J. Fish Dis. 7 107–115 (1984). It has been suggested that the fish gastrointestinal tract serves as a portal entry for V. anguillarum, and that the infection of the fish host begins with the colonization of the posterior gastrointestinal tract and the rectum. (Olsson et al.; J. Fish Dis. 19:225–234 (1996). It has been demonstrated that V.anguillarum exhibits chemotactic mobility towards intestinal mucus, and that motile V. anguillarum cells penetrate crude mucus preparations. Additionally, it has been demonstrated that V. anguillarum adheres to fish intestinal tissue and mucus and to the brush border cells of larval turbot. (Bordas et al.; Appl. Environ. Microbiol. 62:3650–3654 (1996)(Grisez et al.; Dis. Aquat. Org. 26: 181–187 (1996). Following infection of the gastrointestinal tract, it appears that V. anguillarum cells traverse the intestinal epithelium, enter the lamina propria, and spread systemically.

Gastrointestinal mucus is a rich nutrient source that many organisms, including pathogens, can utilize for growth. Studies suggest that growth in mucus is a critical factor to intestinal colonization of a host by pathogens, and that specific physiological changes occur in these bacteria in response to growth in mucus. (Burghoff et al.; Infect. Immun. 61:1293–1300 (1993)(Krivan et al.; Infect. Immun. 60: 3943–3946 (1992). It has been demonstrated that V. anguillarum grows rapidly and efficiently in salmon intestinal mucus. (Garica et al.; Appl. Environ. Microbiol. 63: 1034–1039 (1997). The cells typically exhibit a rapid generation time and express at least five new membrane proteins in mucus-salts medium. Four of the proteins produced during growth in mucus are located in the outer membrane of the cell, while the fifth is located in the cytoplasmic membrane. (Garica et al.; Appl. Environ. Microbiol. 63: 1034–1039 (1997). The present invention provides vaccines and methods for making the same that can be used to prevent vibriosis infection in animals.

BRIEF SUMMARY OF THE INVENTION

Broadly, this invention comprises a live, attenuated strain of V. anguillarum which comprises a mutated mugA gene and method for making the same. The strain is characterized in that it is incapable of expressing a functional mugA protein.

Further, the invention comprises a vaccine strain against V. anguillarum infection in an animal comprising a live, attenuated strain of V.anguillarum wherein the strain is comprised of a mutated mugA gene. The vaccine strain is characterized in that it is incapable of expressing a functional mugA protein.

Another aspect of the invention comprises the method of making and administering the vaccine strain. More particularly, the invention comprises the administration of the vaccine strain to animals selected from the group consisting of fish, bivalves and crustaceans.

In yet another aspect, the invention comprises administering the vaccine strain to animals by immersion, by intraperitoneal injection and oral or anal intubation.

The invention also comprises a method of inducing an immune response in an animal against one or more pathogens which comprises transforming a live, attenuated strain of V. anguillarum having a mutated mugA gene with a plasmid comprising DNA of interest encoding at least one protein antigen for each of the pathogens and administering the transformed strain to an animal.

In yet another aspect, the invention comprises the vaccine strains disclosed herein admixed with a pharmaceutically acceptable carrier. Pharmaceutically acceptable carriers can include water, the culture fluid in which the bacteria are cultured, a solution of physiological salt concentration and diluents selected from the group consisting of stabilizers, carbohydrates, proteins and protein containing agents.

Another aspect of the invention comprises the identification, characterization and sequencing of the mugA gene and the amino acid sequence of the protein encoded by the mugA gene.

In yet another aspect, the invention comprises the use of the mugA gene as a DNA probe to detect the presence of V. anguillarum in animals or media. More particularly, the invention relates to use of the mugA gene as a DNA probe to detect the presence of V. anguillarum in animals selected from the group consisting of fish, bivalves and crustaceans and media selected from the group consisting of sediment and water.

The invention also comprises DNA primers constructed from the mugA gene sequence to be used in polymerase chain reaction (PCR) or reverse transcriptase (RT) or a combination of RT and PCR to detect the presence of V.anguillarum cells, DNA or RNA.

Also within the scope of this invention is the use of the protein encoded by the mugA gene to construct protein subunit vaccines against V.anguillarum infection in animals. Further, the invention comprises the use of antibodies against the mugA protein for the development of passive vaccines against V. anguillarum infection, the treatment of V. anguillarum infection in animals and the development of immunodiagnostic reagents to detect the presence of V. anguillarum in animals or media.

BRIEF DESCRIPTION OF THE DRAWING(S)

FIG. 2 depicts the nucleotide sequence (SEQ ID NO: 1) of the cloned region of DNA containing mugA.

FIG. 3a depicts the putative amino acid sequence (SEQ ID NO: 2) of ORF A/MugA.

FIG. 3b depicts the putative amino acid sequence (SEQ ID NO: 3) of ORF B.

FIG. 3c depicts the putative amino acid sequence (SEQ ID NO: 4) of ORF C/EiaA.

DESCRIPTION OF THE PREFERRED EMBODIMENT(S)

Figure 1:
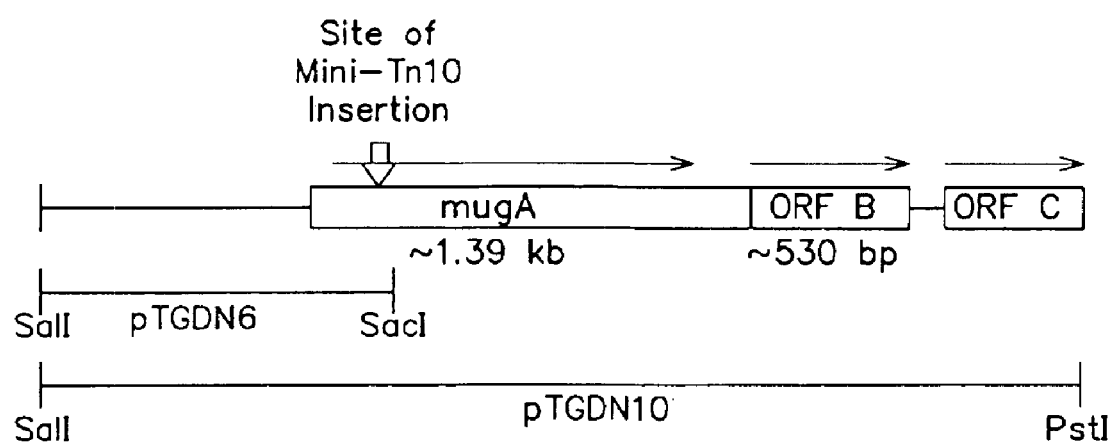
FIG. 1 is a gene map of the cloned region of DNA containing mugA which depicts the nucleotide lengths of the complete open reading frames indicated underneath.

The invention will be described with reference to following non-limiting examples.

MATERIALS AND METHODS

Bacterial Strains, Gowth Conditions, Plasmids, and Preparation of Mucus.

The bacterial strains used are listed in Table 1. *Vibrio anguillarum* M93 (Mitsuru Eguchi, Department of Fisheries, Kinki University, Nara, Japan) is serotype J-O-1. All *V. anguillarum* strains were routinely grown in Luria-Bertani broth +2% NaCl (LB20) supplemented with the appropriate antibiotic, on a rotary shaker at 27° C. Experimental media included: LB20, Marine Minimal Medium (3M), and nine salts solution (NSS) supplemented with 200 μg salmon gastrointestinal mucus protein/ml (NSSM). Garcia et al.; Growth of *Vibrio anguillarum* in salmon intestinal mucus. Appl. Environ. Microbiol. 63: 1034–1039 (1997). All *Escherichia coli* strains were routinely grown in Luria-Bertani broth +1% NaCl (LB10), supplemented with the appropriate antibiotic. *E. coli* CC118 is a lambda lysogen carrying the pir gene required for replication of pLOFKm. The plasmid pLOFKm is a Tn10-based delivery plasmid with kanamycin resistance. Ausubel et al.; Current Protocols in Molecular Biology (1987). Herrero et al.; Transposon vectors containing non-antibiotic resistance selection markers for cloning and stable chromosomal insertion of foreign genes in gram-negative bacteria J. Bacteriol. 172: 6557–6567 (1990). The plasmid pBluescript II SK+ (Stratagene, La Jolla, Calif.) was used as a cloning vector, and pTGDN14 and subclones were pBluescript derivatives. Salmon gastrointestinal mucus was prepared as previously described. Garcia et al.; Growth of *Vibrio anguillarum* in salmon intestinal mucus. Appl. Environ. Microbiol. 63: 1034–1039 (1997). Cell densities for all experiments were determined by serial dilution and plating on LB20 agar plates. Antibiotics were used at the following concentrations for *V. anguillarum*: streptomycin, 200 μg/ml ($Sm^{200}$); kanamycin, 85 μg/ml ($Km^{85}$). Antibiotics were used at the following concentrations for *E. coli*: kanamycin, 40 μg/ml ($Km^{40}$); ampicillin, 100 μg/ml ($Ap^{100}$).

Selection of a Streptomycin-resistant Mutant of *V. anguillarum*

A streptomycin-resistant mutant of *V. angulilarum* M93 was selected by spread plating 100 μl of an overnight culture onto LB20 agar plates supplemented with 100 μg/ml streptomycin. Streptomycin resistant mutants able to grow in media containing 100 μg/ml streptomycin were transferred to LB20+200 μg/ml streptomycin. Mutants able to grow in LB20+200 μg/ml streptomycin were tested for the ability to grow in LB20 and NSSM. A streptomycin-resistant mutant (*V. anguillarum* M93Sm) that exhibited growth rates similar to the parental wild-type strain was selected for farther use. Denkin et al.; Induction of protease activity in *Vibrio anguillarum* by gastrointestinal mucus. Appl. Environ. Microbiol. 65: 3555–3560 (1999).

Transposon Insertion Mutagenesis of *Vibrio anguillarum* M93Sm.

Transposon insertion mutagenesis was employed to create *V. anguillarum* M93Sm mutants, using the mini-Tn10 based transposon vector delivery system developed by Herrero et al. Herrero et al.; Transposon vectors containing non-antibiotic resistance selection markers for cloning and stable chromosomal insertion of foreign genes in gram-negative bacteria. J. Bacteriol. 172: 6557–6567 (1990) Briefly, *V. anguillarum* M93Sm was conjugated with *E. coli* CC118 (λpir)(pLOFKm), which contains the mini-Tn10 (Km'). Aliquots (100 μl) from overnight cultures of each organism were mixed in 2.5 ml NSS plus 2.5 ml 10 mM $MgSO_4$. The suspension of cells was vacuum filtered onto a 0.22μ filter. The filter was placed on an LB15 agar plate (Luria-Bertani agar +1.5% NaCl) and allowed to incubate overnight at 27° C. After incubation the cells on the filter were resuspended in 2.5 ml NSS plus 2.5 ml 10 mM $MgSO_4$, and 100 μl of the cell suspension was spread plated onto LB20 $Sm^{200}$ $Km^{85}$ agar plates and allowed to incubate overnight at 27° C.

Selection of Mucus Growth Mutants.

Colonies derived from the mutagenesis procedure were scraped from the LB20 $Sm^{200}$ $Km^{85}$ agar plates and pooled in 10 ml of NSS. Ten microliters of the *V. anguillarum* cell suspension was added to a carbenicillin counter-selection medium containing 50 ml NSS supplemented with 300 μg/ml mucus protein plus streptomycin (200 μg/ml), kanamycin (85 μg/ml) and carbenicillin (250 μg/ml). Cells were incubated in this counter selection medium at 27° C. for 3 h. After incubation, the cells were removed from the counter-selection medium by centrifugation (12,000×g, 30 min). The cells were washed twice in NSS, resuspended in 50 ml of LB20 plus $Sm^{200}$ $Km^{85}$ and allowed to grow overnight on a rotary shaker at 27° C. After growth, the cells were put through two more rounds of carbenicillin counter-selection. After the third round of selection, cells were washed free of the counter-selection medium and 100 μl aliquots were spread onto LB20 $Sm^{200}Km^{85}$ agar plates. Isolated colonies were screened on LB20 $Sm^{200}Km^{85}$ plates and mucus agar $Sm^{200}Km^{85}$ plates (300 μg/ml mucus protein). Colonies that did not grow on mucus agar plates were retained.

Southern DNA Transfer, Hybridization Analysis and DNA Probes.

For all Southern analysis, total genomic DNA was extracted from bacteria and digested to completion with PstI (Promega, Madison, Wis.). The resulting fragments were loaded in equal amounts on an agarose gel and were separated by agarose gel electrophoresis (0.8% agarose gel, 70 V) in Tris acetate buffer. DNA samples were transferred from the agarose gel to a nylon membrane (MagnaGraph, MSI, Westboro, Mass.) for Southern hybridization analysis (15 h hybridization at 60° C.). Ausubel et al.; Current Protocols in Molecular Biology (1987).

To confirm the mini-Tn10 insertion in *V. anguillarum* M93Sm chromosomal DNA, blots were probed with a digoxigenin-dUTP labeled kanamycin cassette. Briefly, the kanamycin cassette probe was constructed by digesting the pUC4K plasmid (Pharmacia Biotech, Piscataway, N.J.) with PstI. The resulting fragments were separated by agarose gel electrophoresis, and the 1.24 kb kanamycin cassette was purified from the agarose gel using a Geneclean Spin Kit (Bio 101, Vista, Calif.). The kanamycin cassette was then labeled with digoxigenin-dUTP using a DIG High Prime DNA Labeling and Detection Starter Kit II (Boehringer Mannheim, Germany) according to the instructions of the manufacturer.

To screen for the presence of the mugA gene in *V. anguillarum* and other bacteria, blots were probed with a digoxigenin-dUTP labeled mugA gene probe. Briefly, primers were derived from the sequence of the mini-Tn10 interrupted gene as mugA-forward (5'TTTCTGCAGC-TGGTTGAAATAACTCAAGGCC-3' (SEQ ID NO: 5)) and mugA-reverse (5'-TTTCTGCAGGGATCCGAAA-CGGAAGGCTTCGC-3' (SEQ ID NO: 6)) (Gibco BRL). A 1.4 kb DNA fragment of the mugA gene was PCR amplified from *V. anguillarum* genomic DNA using the primers and a PCR-DIG Probe Synthesis Kit (Boehringer Mannheim, Germany) according to the instructions of the manufacturer. PCR conditions are indicated below.

Cloning and Mapping of the mugA::mini-Tn10 Region of DNA.

Initially, the gene fragment containing the mini-Tn10 mugA, was cloned and sequenced. Total genomic DNA was extracted from *V. anguillarum* M93SmΩD and digested to completion with PstI. The cloning vector pBluescript (Stratagene) was digested with PstI (Promega, Madison, Wis.), treated with calf intestinal phosphatase (Promega, Madison, Wis.), and ligated (1 U/µl DNA ligase; Promega, Madison, Wis.) to the PstI digested genomic DNA. Plasmid DNA containing genomic DNA was then transformed into the competent *E. coil* host (XLI MRF', Km$^s$). Ausubel, F. M. et al.; Current Protocols in Molecular Biology (1987). Transformants were screened for the presence of the transposon-interrupted gene by plating onto LB Km$^{40}$ plates. Plasmid DNA of transformants exhibiting kanamycin resistance was extracted by pelleting 1–3 ml *E. coil* cells (~2.0×10$^9$ cells/ml), resuspending the cell pellet in 200 µl Cell Resuspension Solution (50 mM Tris-HCl pH 7.5, 10 mM EDTA, 100 µg/ml RNAse A), lysing the cells in 200 µl Cell Lysis Solution (0.2 M NaOH, 1% SDS), neutralizing the lysate with Neutralization Solution (1.32 M potassium acetate, pH 4.8) and isolating plasmid DNA using a Wizard Minicolumnn (Wizard Mini-Preps kit, Promega, Madison, Wis.). The cloned mini-Tn10 interrupted gene was mapped by digesting the cloned DNA with various restriction enzymes followed by electrophoresis and analysis of the resulting fragments on a 0.8% agarose gel. Restriction enzymes used for mapping include PstI, EcoRI, EcoRV, BamHI, HindIII, SalI, SacI, SpeI, HincII, ClaI, KpnI SmaI, XhoI, BalI, BstXI, NotI, XbaI, and StyI (Promega, Madison, Wis.). Subcloning was performed as described in the Results section of this report to obtain smaller DNA fragments for DNA sequencing.

To obtain the wild-type mugA gene, total genomic DNA of *V. anguillarum* M93Sm was extracted and digested to completion with HindIII (Promega) and BamHI (Promega), ligated to HindIII and BamHI digested pBluescript, and transformed into *E. coli* (XLI MRF$^+$). Transformants were plated on LB10 Amp$^{100}$ plates containing isopropylthioga-lactoside (IPTG; 100 mM) and 5-Bromo-4-chloro-3-indoyl-β-D-galactopyranoside (X-Gal; 80 g/ml)(BIO-RAD laboratories, Richmond, Calif.) and allowed to incubate overnight at 37° C. Plating on the medium allowed for blue (lac$^+$)—white (lac$^-$) screening for inserts in the lacZ gene of pBluescript. White ampicillin resistant colonies were transferred to fresh LB10 Amp$^{100}$ plates, allowed to grow overnight at 37° C., and blotted onto nylon membranes. Colony blots were performed as previously described (4), using the digoxigenin-dUTP labeled mugA gene as a probe. Colonies that hybridized to the mugA probe were screened by PCR analysis, using the mugA forward and reverse primers described above. DNA sequence analysis revealed that this yielding a 2 kb fragment containing all but the last 113 bp of the mugA gene. The entire wild-type mugA gene was obtained following PCR amplification from *V. anguillarum* M93Sm using the mugA-forward primer (described above) and mugA-reverse2 primer (5'TTTAAGCTTCACGC-ATGTAAATACTTGCC-3' (SEQ ID NO: 7)).

PCR Conditions and DNA Sequencing.

The same conditions were employed for all genomic and plasmid DNA samples to be amplified by PCR. All samples were amplified using Taq polymerase (3.5 U/100 µl reaction mixture; Gibco BRL Life Technologies, Bethesda, Md.) on a Perkin Elmer GeneAmp Model 9600 Thermocycler (Perkin Elmer Cetus, Norwalk, Conn.). PCR cycle conditions were: 94° C., 1 min; 51° C., 2 min; 72° C., 3 min. The reaction was run for 35 cycles and then held at 4° C. until collected. All DNA sequencing was performed by the W.M. Keck Laboratory at Yale University, New Haven, Conn. The DNA was sequenced using Taq FS DNA polymerase and fluorescent-dideoxy terminators in a cycle sequencing method and the resultant DNA fragments were electophoresed and analyzed using an automated Applied Biosystems 377 DNA sequencer.

Fish Infections.

All fish infection experiments were carried out for a period of 21 d. *V. anguillarum* cells were prepared overnight by culture in LB20 overnight with shaking (27° C.) to a density of ~2×10$^9$ CFU/ml. Cells were harvested by centrifugation, washed twice in NSS, resuspended in NSS, and diluted to the appropriate inoculation concentrations. Prior to inoculation, Juvenile Atlantic salmon (*Salmo salar*) were anesthetized in water supplemented with tricaine methane sulfonate (75 g/L). Fish were injected intraperitoneally with equal volumes (50 µl) of either NSS alone (control fish) or cells resuspended in NSS. Plate counts were performed to determine the actual number of cells injected. Fish were maintained in 2 m diameter, 200 liter tanks partially submerged in flowing water to maintain tank temperatures at ~15° C. throughout the experiment. Death due to vibriosis was determined by the observation of gross clinical signs (including, but not limited to, observation of petechiac, hemorrhaging through the vent, presence of lesions in the walls of the abdomen) of the disease and recovery of *vibrio* (*V. anguillarum* M93) or streptomycin resistant *vibrio* (*V. anguillarum* M93Sm) or streptomycin and kanamycin resistant *vibrio* (*V. anguillarum* M93SmΩD) from dead fish. Challenge of fish surviving *V. anguillarum* M93SmΩD infection commenced 7 d after conclusion of the initial fish infection experiment and was performed using the same procedure, under the previously described conditions.

Computer Analysis of DNA and Amino Acid Sequences.

Open reading frames were determined from the nucleotide sequence using ORF Finder. www.ncbi.nlm.nih.gov/gorf/gorf.html.;Altschul et al.; Gapped BLAST and PSI-BLAST: a new generation of protein database search programs. Nucleic Acids Res. 25: 3389–3402 (1997). Putative promoters were determined using Promoter Prediction. Reese, M. G.;Diploma Thesis. German Cancer Research Center, Heidelberg, Germany (1994); Reese et al; Novel Neural Network Algorithms for Improved Eukaryotic Promoter Site Recognition. The Seventh International Genome Sequencing and Analysis Conference, Hilton Head Island, S.C. (1995); Reese et al.; Large Scale Sequencing Specific Neural Networks for Promoter and Splice Site Recognition. Biocomputing: Proceedings of the 1996 Pacific Symposium. World Scientific Publishing Co., Singapore (1996). BLASTn and BLASTp searches were performed to determine nucleotide and protein sequence similarities. Altschul et al.; Gapped BLAST and PSI-BLAST: a new generation of protein database search programs. Nucleic Acids Res. 25: 3389–3402. (1997) Probable subcellular localization of putative proteins was determined using PSORT. Nakai et al; Expert system for prediction protein localization sites in Gram-negative bacteria, PROTEINS: Structure, Function, and Genetics. 11: 95–110 (1991). Database searches for amino acid composition similarities were performed using Propsearch and AACompIdent Tool (ExPASy Server). Hobohm, et al.; A sequence property approach to searching protein databases. J. Mol. Biol. 251: 390–399 (1995); Wilkins et al.; Protein Identification and Analysis Tools in the ExPASy Server in: 2-D Proteome Analysis Protocols. (1998).

RESULTS

Growth of *V. anguillarum* M93Sm and M93SmΩD in LB20 and Mucus Medium.

The procedure for the construction and selection of mini-Tn10 insertion mutants of *V. anguillarun* M93Sm unable to grow on mucus agar plates was performed as described in the Materials and Methods. One insertion mutant, *V. anguillarum* M93SmΩD, which grew on LB20 Sm$^{200}$ Km$^{85}$ agar and exhibited no growth on mucus agar plates (300 μg/ml mucus protein) was selected and used. Referring to Table 2, the growth of M93SmΩD was observed in LB20 and NSSM and compared to the growth of M93Sm in identical media *V. anguillarum* M93Sm and M93SmΩD grew to comparable levels in LB20 after 24 h (~4–6×10$^9$ CFU/ml), with CFU increases of about 1600 fold and 1900 fold, respectively. In NSSM, M93Sm grew to a maximum CFU of >4.6×10$^9$ CFU/ml in 10 h and subsequently declined to ~1.4×10$^9$ CFU/ml by 24 h. This decline in viability following growth in mucus was previously reported by Garcia et al. Garcia et al.; Growth of *Vibrio anguillarum* in salmon intestinal mucus. Appl. Environ. Microbiol. 63: 1034–1039 (1997). In contrast, M93SmΩD failed to grow in mucus over a 24 h incubation. The cell density declined 18-fold from 2.13×10$^6$ CFU/ml to 1.16×10$^5$ CFU/ml.

Determination of Mini-Tn10 Insertion by Southern Analysis.

In order to confirm that the *V. anguillarum* M93SmΩD genome contained a mini-Tn10 insertion, PstI digested genomic DNA from *V. anguillarum* M93Sm and M93SmΩD were each probed with a dUTP-digoxigenin labeled kanamycin cassette. Unlabeled kanamycin cassette (1.3 kb) was hybridized with the probe as a control. Southern analysis of the genomic DNA revealed a hybridizable 11 kb fragment in M93SmΩD. No hybridizable fragments were observed in the M93Sm genomic DNA. The results demonstrate that the transposon was present in the M93SmΩD genomic DNA as a single copy.

Cloning Subcloning, and Sequencing of the Transposon-interrupted Gene.

Since Southern analysis had shown that the mini-Tn10 insertion was contained within an 11 kbp fragment, PstI digested DNA from *V. anguillarum* M93SmΩD was ligated with PstI-digested pBluescript SKII and transformed into *E. coli* XLI MRF'. Transformants were selected on LB10 Amp$^{100}$ Km$^{40}$ plates. Restriction endonuclease analysis of a pBluescript-derived plasmid conferring kanamycin resistance demonstrated that the plasmid contained an 11 kbp PstI-PstI fragment (pTGDN14).

In order to obtain smaller fragments for sequencing, this plasmid was subjected to further restriction endonuclease analysis and subcloning. Referring to FIGS. 1, 2, and 3a–c, the plasmid pTGDN14 was digested with SalI and SacI, and a 3.1 kb fragment of DNA containing the mini-Tn10 insert was isolated and ligated to SalI and SacI digested pBluescript, yielding pTGDN6. Additionally, pTGDN14 was digested with SalI and religated, to eliminate a 4.2 kbp SalI-SalI fragment of *V. anguillarum* DNA. The resulting subclone was termed pTGDN10. The pTGDN10 construct consisted of 7 kbp of DNA containing the mini-Tn10 insertion in a SalI-PstI fragment ligated to pBluescript. Sequencing was performed by primer walking from the T7 promoter to the mini-Tn10 insert on pTGDN6, and from the mini-Tn10 insert on pTGDN10 outwards toward the T3 promoter. A map and sequence of the region of DNA containing the mini-Tn10 insert is presented in FIG. 1. The regions of the two subclones that were sequenced are indicated. The putative amino acid sequences of the three ORFs are shown in FIGS. 3a–c. Open reading frames depicted in FIG. 1 are indicated as shaded boxes, with nucleotide lengths for complete ORFs indicated underneath. Directions of transcription are indicated by horizontal arrows. The transposon insertion site is indicated by a vertical arrow. Subclones utilized for sequencing are indicated. The entire 3.59 kb nucleotide sequence is depicted in FIG. 2. Proposed promoter sites are underlined and indicated with a curved arrow. Putative Shine-Delgarno sequences are labeled (S-D) and underlined. Start codons for each ORF are underlined and indicated by horizontal arrows followed by the ORF name. Stop codons are underlined and indicated with an asterisk. The sequence of ORF C is incomplete and no stop codon is indicated. The transposon insertion site is indicated with a bold vertical arrow.

The entire wild-type mugA gene was obtained following PCR amplification from *V. anguillarum* M93Sm using the mugA-forward primer and mugA-reverse2 primer. Utilization of the mugA-reverse2 primer allowed PCR amplification of the entire mugA gene, including the last 113 bp of the mugA gene, which is not amplified when using the mugA-reverse1 primer. Thus, while the PCR product generated using the mugA-forward and mugA-reverse1 primers is ~1.4 kb, the PCR product generated using the mugA-forward and mugA-reverse2 primers is s approximately 1.5 kb.

Screening of Chromosomal DNA from Various Bacteria Using mugA as a DNA Probe.

Southern hybridization analysis was employed to determine whether the mugA gene was present in bacteria other than *V. anguillarum* M93. Genomic DNA from *V. anguillarum* strains M93Sm, NB10 and 2129 and *E. coli* ATCC 25922 was probed with the mugA DNA probe. Milton et al.; Flagellin A is essential for the virulence of *Vibrio anguillarum*. J. Bacteriol. 178: 1310–1319 (1996); Garcia et al.; Growth of *Vibrio anguillarum* in salmon intestinal mucus. Appl. Environ. Microbiol. 63: 1034–1039 (1997). Unlabeled mugA (1.4 kb) was hybridized with the probe as a control. All strains of *V. anguillarum* tested showed a single band of hybridizing DNA at approximately 9.5 kbp. No hybridizing DNA was observed in *E. coli* ATCC 25922, nor were hybridizing bands observed when DNA from *Aeromonas hydrophila, A. salmonicida, V. carcariae,* and *V. parahemolyticus* were probed with mugA.

Fish Infection Studies.

As depicted in Table 3, the virulence of *V. anguillarum* wild type (M93) and mutant strains (M93Sm and M93SmΩD) were compared by injecting various concentmutation conferring streptomycin resistance affected virulence. No mortalities were observed in fish injected with NSS alone. All fish injected with $10^6$, $10^7$ and $10^8$ *V. anguillarum* M93 and M93Sm cells died in 1–3 days. These data demonstrated that the virulence of *V. anguillarum* M93 and the streptomycin-resistant derivative *V. anguillarum* M93Sm were similar. In contrast, no fish died following trations of cells intraperitoneally into Atlantic salmon (Table 3). The virulence of *V. anguillarum* M93 (wild type) was compared to M93Sm (Sm$^r$ mutant) to determine whether the injection with *V. anguillarum* M93SmΩD at any of the doses administered.

As depicted in Table 4, to determine whether injection with *V. anguillarum* M93SmΩD provided protection to fish against vibriosis caused by a virulent strain, Atlantic salmon that survived injection with *V. anguillarum* M93SmΩD were challenged with lethal doses of *V. anguillarum* M93Sm (Table 4). The unvaccinated (control) fish were from the same stock and were the same age as the vaccinated fish. All unvaccinated control fish inoculated with *V. anguillarum* M93Sm at concentrations of $10^6$ and $10^5$ cells died in 2 days and 4 days, respectively. One of five fish died in 4 days when inoculated with $10^4$ cells. In contrast, no vaccinated fish died following injection of $10^6$ and $10^5$ *V. anguillarum* M93Sm cells. These data demonstrate that prior inoculation of Atlantic salmon with the avirulent *V. anguillarum* M93SmΩD is protective against vibriosis caused by the virulent M93Sm.

TABLE 1

Bacterial strains.

| Species and Strains | Description |
| --- | --- |
| *V. anguillarum* | |
| M93 | wild type |
| M93Sm | streptomycin-resistant (Sm$^r$) mutant of M93 |
| M93SmΩD | M93 (mugA::Tn10), Sm$^r$ Km$^r$ |
| NB10 | wild type |
| 2129 | wild type |
| *E. coli* | |
| CC118 | (Δ(ara-leu) araD ΔlacX74 galE galK phoA20 thi-1 RpsE rpoB argE(Am) recA1) |
| XLI MRF' | cloning vector host strain |
| ATCC 25922 | wild type |
| A. hydrophila | wild type |
| A. salmonicida | wild type |
| V. carcariae | wild type |
| V. parahemolyticus | wild type |

TABLE 2

Growth of *Vibrio anguillarum* M93Sm and M93SmΩD in LB20 and NSSM (200 μg mucus)$^a$

| Time (h) | CFU/ml LB20 | | NSSM | |
| --- | --- | --- | --- | --- |
| | M93Sm | M93SmΩD | M93Sm | M93 SmΩD |
| 0 | 3.73 (± 0.25) × $10^6$ | 2.03 (± 0.32) × $10^6$ | 2.53 (± 0.31) × $10^6$ | 2.13 (± 0.21) × $10^6$ |
| 10 | 4.67 (± 0.37) × $10^9$ | 1.40 (± 0.35) × $10^9$ | 4.67 (± 1.50) × $10^9$ | 4.73 (± 0.45) × $10^5$ |
| 24 | 6.00 (± 0.20) × $10^9$ | 3.90 (± 0.46) × $10^9$ | 1.43 (± 0.12) × $10^9$ | 1.16 (± 056) × $10^5$ |
| Fold Change (0–24 h) | 1596 increase | 1921 increase | 565 increase | 18 decrease |

$^a$Cells were grown overnight in LB20 (27° C.) with shaking and prepared for inoculation into LB20 or NSSM as described in the Materials and Methods section. Cell density was determined by serial dilution of samples and plating onto LB20 agar as described in the Materials and Methods section. All cell density determinations were done in triplicate.

TABLE 3

Comparison of virulence of *V. anguillarum* M93, *V. anguillarum* M93Sm, and *V. anguillarum* M93SmΩD in Atlantic salmon$^a$

| Strain | Approximate Dose/fish (CFU) | Mortality | Time of death due to vibriosis |
| --- | --- | --- | --- |
| *V. anguillarum* M93 | $10^6$ | 4/4 | 1 d |
| | $10^7$ | 5/5 | 1 d |
| | $10^8$ | 5/5 | 1 d (4/5), 2 d (5/5) |
| *V. anguillarum* M93Sm | $10^6$ | 4/4 | 2 d (3/4), 3 d (4/4) |
| | $10^7$ | 5/5 | 1 d |
| | $10^8$ | 5/5 | 1 d |
| *V. anguillarum* M93SmSD | $10^6$ | 0/4 | NA |
| | $10^7$ | 0/5 | NA |
| | $10^8$ | 0/5 | NA |

$^a$*V. anguillarum* cells were prepared by growing in LB20 overnight (27° C.) to a density of 2 × $10^9$ CFU/ml. Cells were harvested by centrifugation, washed twice in NSS, resuspended in NSS, and diluted to the appropriate inoculation concentrations. All fish were injected IP with equal volumes (50 μl) of either NSS alone (control fish) or cells resuspended in NSS. Plated counts were performed to determine the actual number of cells injected. The experiment continued for 21 d. No mortalities were observed in control fish throughout the 21 d period. Death due to vibriosis was determined by examination of clinical signs and recovery of vibrio (*V. anguillarum* M93), streptomycin resistant vibrio (*V. anguillarum* M93Sm) or streptomycin and kanamycin resistant vibrio (*V. anguillarum* M93SmΩD).

TABLE 4

Challenge of *V. anguillarum* M93SmΩD infection survivors with lethal doses of *V. anguillarum* M93Sm[a]

| Fish | Approximate Dose/fish (CFU) | Mortality | Time of death due to vibriosis |
|---|---|---|---|
| Unvaccinated fish[b] | $10^4$ | 1/5 | 4 d |
|  | $10^5$ | 5/5 | 4 d |
|  | $10^6$ | 5/5 | 2 d |
| Vaccinated fish | $10^5$ | 0/5 | NA |
|  | $10^6$ | 0/5 | NA |

[a]*V. anguillarum* cells were prepared by growing in LB20 overnight (27° C.) to a density of $2 \times 10^9$ CFU/ml. Cells were harvested by centrifugation, washed twice in NSS, resuspended in NSS, and diluted to the appropriate inoculation concentrations. All fish were injected IP with equal volumes (50 μl) of either NSS alone (control fish) or cells resuspended in NSS. Plated counts were performed to determine the actual number of cells injected. The experiment continued for 21 d. No mortalities were observed in control fish throughout the 21 d period. Death due to vibriosis was determined by examination of clinical signs and recovery of streptomycin resistant vibrio (*V. anguillarum* M93Sm).
[b]Unvaccinated control fish are from the same stock and are the same age as the vaccinated fish.

DISCUSSION

Both the region of DNA containing the transposon insertion and a wild type version of that region were cloned and sequenced. Approximately 2.5 kbp of the sequenced region contained 3 ORFs. The ORF encoding mugA is 1.39 kbp in length and encodes a putative protein of 51.6 kDa (463 amino acids) with a pI of 5.24. Referring to FIG. 2, a proposed promoter site and a ribosomal binding site was located 146 bp and 5 bp upstream from the ATG start codon of the mugA gene. Milton et al.; Flagellin A is essential for the virulence of *Vibiro anguillarum*. J. Bacteriol. 178: 1310–1319 (1996); Reese, M. G.; Diploma Thesis. German Cancer Research Center, Heidelberg, Germany (1994); Reese et al., Novel Neural Network Algorithms for Improved Eukaryotic Promoter Site Recognition. The Seventh International Genome Sequencing and Analysis Conference, Hilton Head Island, S.C. (1995); Reese et al.; Large Scale Sequencing Specific Neural Networks for Promoter and Splice Site Recognition. Biocomputing: Proceedings of the 1996 Pacific Symposium. World Scientific Publishing Co., Singapore (1996). The nucleotide sequence shows no significant homology to any known sequence in Genbank. The amino acid sequence shows homology to *Enterococcus faecium* aggregation substance (27% identity, 42% similarity) in 109 amino acids toward the C-terminal end of MugA, and to myosin from several organisms, the most significant of which was from human skeletal muscle (22% identity, 38% similarity) over 319 amino acid residues. However, the MugA amino acid sequence demonstrated no significant homology to other bacterial proteins over the entire sequence.

The mugA gene probe only hybridized with DNA from strains of *V. anguillarum*, including M93, 2129 and NB10. Additionally, the PstI fragments with which it hybridized were approximately the same size in all strains (~9.5 kb). No hybridizing DNA fragments were found in several other fish pathogens tested, including *V. carchariae, V. parahemolyticus, A. salmonicida*, and *A. hydrophila*.

A second open reading frame, ORF B, is 530 bp in length and has an ATG stat codon 16 bp immediately downstream of the mugA stop codon. A predicted ribosomal binding site is located 7 bp upstream from the start codon of ORF B. This ORF encodes for a putative protein of 18.6 kDa (176 amino acids) with a pI of 4.17. Database searches using the nucleotide and amino acid sequence show no significant homology to known sequences in GeneBank. Additionally, no similarities to other protein families were found when a database search was conducted based on amino acid composition.

A third open reading frame, ORF C, is located 144 bp downstream of ORF B. A putative promoter and a ribosome binding site are located at 23 bp and 8 bp upstream from the ATG start codon, respectively. A database search using the incomplete nucleotide sequence (352 bp) showed no significant homology to known nucleotide sequences in Genbank. However, the amino acid sequence exhibits very strong similarity to a putative 19.5 kDa protein of unknown function from the fish pathogen *Edwardsiella ictaluri* (52% identity, 67% similarity), the causative agent of the disease enteric septicemia of catfish. ORF C has been termed eiaA (*E. ictaluri*-like antigen A). The ORF C amino acid sequence also showed strong similarity to an unknown hypothetical protein from *E. coli* (30% identity, 56% similarity). Database searches using the combined attributes of amino acid composition, molecular weight and pI found no similarities to other protein families.

While *V. anguillarum* M93 and M93Sm are highly virulent strains causing 100% mortality at doses of $10^5$ CFU/fish, M93SmΩD is avirulent even when $10^8$ CFU are injected IP (Tables 2 and 3). An equivalent dose ($10^8$ CFU) of *V. anguillarum* M93Sm killed all fish within 1 day. No mortalities and no evidence of vibriosis were observed over a 21 d period in fish injected with M93SmΩD. While IP injection is an artificial route of infection, these data demonstrate that the ability of *V. anguillarum* to grow in mucus affects the virulence of this organism. Additionally, fish previously injected with *V. anguillarum* M93SmΩD were completely protected against vibriosis when challenged with lethal doses ($10^5$ and $10^6$ cells injected/fish) of the virulent *V. anguillarum* M93Sm. All fish that were not previously inoculated with M93 SmΩD died 2–4 days after challenge at these doses.

Typical procedures for the construction of a subunit vaccine using mugA, the purification of anti-MugA antibodies, the utilization of anti-MugA antibodies for immunodetection of *V. anguillarum* and the passive immunization of fish using anti-MugA antibodies follow. Such procedures are well within the skill of the art.

Construction of a Subunit Vaccine Using mugA

Clone mugA gene into an inducible expression vector to construct a gene/protein fusion between mugA and a portion of another gene, which permits rapid purification of the mugA protein (MugA). Examples of such vectors include: Glutathione S-transferase (GST) gene fusion vectors (e.g. pGEX vectors—available from Amersham Phamacia Biotech) and calmodulin-binding peptide (CBP) vectors (e.g. pCAL vectors—available from Stratagene). The fusion proteins generated with these vectors allow the target protein to be purified by an affinity column using the fusion protein tag (GST or CBP) to bind to glutathione or calmodulin, respectively. Specific proteases are available to remove the protein purification tag from mugA. The proteases used to remove the protein purification tag include thrombin, Factor Xa, enterokinase protease, and prescission protease. The purified MugA protein can be mixed with an adjuvant to improve the antigenic response of the immunized animal. Adjuvants used in fish include Alum [Al(OH)$_3$] and mineral oil. The vaccine can be administered to the fish by injection.

Purification of Anti-MugA Antibodies

MugA, purified as described above and combined with an adjuvant as described above, will be injected into rabbits.

The rabbits can be injected three times at two-week intervals to boost antibody production. Similar methods may be used to immunize other animals (i.e. goats, fish, etc.). Two weeks after the third injection, blood from the rabbits (or other immunized animals) can be collected. The antibody containing serum can be separated from the blood cells by low speed centrifugation and antibodies purified from the serum using affinity column chromatography employing either Sepharose-Protein A or -Protein G to bind the antibodies. Affinity purified antibodies can be further purified to yield anti-MugA antibodies by affinity binding to Sepharose-MugA columns. Sepharose-MugA is created by reacting purified MugA protein with cyanogen bromide activated Sepharose.

Utilization of Anti-MugA Antibodies for Immunodetection of *V. anguillarum*

Samples (tissue or water) containing suspected *V. anguillarum* can be reacted with anti-MugA antibodies. After a series of washes to remove any unreacted primary antibody, a second antibody reactive against rabbit antibodies (e.g. goat-anti-rabbit IgG) tagged with a detection reagent (e.g. FITC or alkaline phosphatase) can be added to the primary antibody-sample mixture. After reaction and washes to remove unreacted secondary antibody, the presence of MugA can be detected using the specific detection reagent on the secondary antibody.

Passive-immunization of Fish Using Anti-MugA Antibodies

Animals to be passively immunized against *V. anguillarum* infection can be injected with a suspension of purified anti-MugA antibody. For best results, the antibodies can be made and purified from the same species as that being passively immunized. The use of same species antibody prevents immune reactions against the immunizing antibodies by the target animals.

All journal articles and reference citations provided above, in parentheses or otherwise, whether previously stated or not, are incorporated herein by reference.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

I claim:

1. A live, attenuated strain of *V.anguillarum* which comprises:
   a mugA gene comprising nucleotides 1218–2610 of SEQ ID NO:1, the strain having a mutation located within nucleotides 1218–2610 of SEQ ID NO: 1 that renders the strain incapable of expressing a functional mugA protein.

2. The live, attenuated strain according to claim 1 wherein the strain is incapable of growing in salmon intestinal mucus.

3. The live, attenuated strain according to claim 1 wherein the mutation is non-revertible.

4. The live, attenuated strain according to claim 2 wherein the mutation is an insertion.

5. The live, attenuated strain according to claim 2 wherein the mutation is a deletion.

6. A vaccine strain against *V.anguillarum* infection in an animal selected from the group consisting of fish, bivalves and crustaceans comprising:
   a live, attenuated strain of *V.anguillarum* which comprises a mugA gene comprising nucleotides 1218–2610 of SEQ ID NO:1, the strain having a mutation located within nucleotides 1218–2610 of SEQ ID NO: 1 that renders the strain incapable of expressing a functional mugA protein.

7. The vaccine strain according to claim 6 wherein the strain further comprises a pharmaceutically acceptable carrier.

8. The vaccine strain according to claim 6 wherein the mutation is non-revertible.

9. The vaccine strain according to claim 8 wherein the mutation is an insertion.

10. The vaccine strain according to claim 8 wherein the mutation is a deletion.

11. A method for immunizing an animal selected from the group consisting of fish, bivalves and crustaceans against *V. anguillarum* infection in the animal which comprises:
    administering to the animal a vaccine comprised of a live, attenuated strain of *V.anguillarum* which comprises a mugA gene comprising nucleotides 1218–2610 of SEQ ID NO:1, said strain having a mutation located within nucleotides 1218–2610 of SEQ ID NO: 1 that renders the strain incapable of expressing a functional mugA protein.

12. The method according to claim 11 wherein administering comprises immersion.

13. The method according to claim 11 wherein administering comprises intraperitoneal injection.

14. The method according to claim 11 wherein administering comprises oral intubation.

15. The method according to claim 11 wherein administering comprises anal intubation.

16. The method according to claim 11 wherein administering comprising immersing the animal in a medium containing the attenuated strain.

17. The method according to claim 11 wherein the mutation in the mugA gene is non-revertible.

18. The method according to claim 17 wherein the mutation in the mugA gene is an insertion.

19. The method according to claim 17 wherein the mutation in the mugA gene is a deletion.

20. A method of inducing an immune response in an animal selected from the group consisting of fish, bivalves and crustaceans against one or more pathogens which comprises transforming a live, attenuated strain of *V. anguillarum* which comprises a mugA gene comprising nucleotides 1218–2610 of SEQ ID NO:1 said strain having a mutation located within nucleotides 1218–2610 of SEQ ID NO: 1 that renders said strain incapable of expressing a functional mugA protein, with a plasmid comprising DNA of interest encoding at least one protein antigen for each of the pathogens and administering the transformed strain to the animal.

* * * * *

SEQUENCE LISTING

```
<160> NUMBER OF SEQ ID NOS: 4

<210> SEQ ID NO 1
<211> LENGTH: 3588
<212> TYPE: DNA
<213> ORGANISM: Vibrio anguillarum
<220> FEATURE:
<221> NAME/KEY: modified_base
<222> LOCATION: (3572)
<223> OTHER INFORMATION: a, t, c, g, other or unknown

<400> SEQUENCE: 1
gtcgacttat tgcattgatg gcgtacatgg tagtgccatc cttcgtttgc taacaagcgt     60
tgtataaaag cttggtcggt ttcatcaagt tgaacacaat actcatgatt tttcccactt    120
ccggaaaggg aaaagtgaaa atagcttttg agatcagcct gttctagcag cttttcaatg    180
atctttttcg tcgttacgtt ttgaaaaatc tgacgactgc gtttgtattg caacaagcta    240
agtggatcca atatctctat ttgataataa aactgctgct tgtctttgct atatcctgtg    300
aattgcagag tgctacatat acctgaaaaa aaacgctttc cagaatctaa ttcgtaagac    360
acacaaacag ctttacctag gtttttggta tcgatctcca tgtttgccgc gatggaaacg    420
gaaaactgac acccgccgga tacgctttcc tctccgatta attgcgtgac aatataactt    480
ttgctatctg aaagcttaat ggtgagggag cgggtttggt gctttaattc gttactgctc    540
atattcaatt aattcactat taaataaaca gttctaaaag gctgtttatt ggatgaatat    600
tcgaaattat cacataataa ttgatgctat tattacttgc tgtattggta tcaactttca    660
tgctctatac atgtaatata tttcgagtta gaccttaatt caaggtaatt tgtctattta    720
attattatct gaataatatg taatcgattg ctttgtggtt atttttatgt ttgtttcatt    780
tttaatgacg gtgagcttgt gcattcatat tttttatgat gacaacatct ttgatgaagt    840
atttaagata ttgttaatgc atgaggggtt tgcgtgtatt ttttatatta aatcataata    900
aaatcaacaa tatatgttat tttgtgtctt tttatagtgt tcttttaaag aggtaggatg    960
acctaaaggt cgcctaaata tggcgtaaat tgccattgct ataattcacc tcaaagatac   1020
```

```
actattggca aattgacaaa tatgtcactt cgtatgaaac aatattagta gatgttgttt    1080
ttgctgcaaa aataaaaatt tttctggttg aaataactca aggcctctag cgttttcctt    1140
tatcttaaaa tacaggaaat agcgattgaa gttaattgac acttaagcaa atagtcaacc    1200
taacagagca ggaacctatg cctttgtcaa agcatcaaat tgagcaactt tctaaacctc    1260
tgagtgatga ttcgatctgt ggcgtttatc ttaaactgga aaaaagtgct tttcgcccat    1320
tacgtaatga atttaatgtc gcgcaaactg cgctgcgtaa gctaagtcaa aaccctagtg    1380
ctgacgagag agatgcgtta caagaggcat gtctaaataa gtggaagatt ctctctgaca    1440
gtttgtacga acagttttca aaaacaacca gagatatcga gctcatctca tggtttgttg    1500
ctgctcaatt ccttctcgat accacattag aaagtgctgc aatagccttg agtggttag    1560 cggatttaag tgagaagcac tgggatcacc tcaaccctgt actaccagtt gaaacgctca    1620
aatctgatga tgataagggc aaagaaagag agcaagcaga tgcgaaagtt aaagcatttt    1680
tccaactagt cggcgatagc gaggaaagct cgattctcta tgcgccggtg ctgcaactgc    1740
ccttagtcgg ggaagtgacg tttttttgact ttcaaagtgc agagagaaaa ggcgaaatca    1800
gccaactgaa atctatgctt acgaccacgg tggcgcaaga gcgtttcgca attcaattca    1860
agatggaaaa cgccaaacgt tgtgtcaccc aattagatcg tttgtcagcg ttggtgagca    1920
ctaagtgtca ttctctaggc agtcaaagta ccaacttcgg atttgcgaag tcactgctta    1980
cccgtgttga aaacgctttg gttcatctaa gtggaattaa gttagcaccg aaagcggagg    2040
ccaagacagt agagcaagag gttgccgaaa gttcagtttc tgaaggggag ctgccaagcc    2100
atatggatac aaaacatata gagcgaatac cgatggcatc agagcaggct cagaccgtaa    2160
gccaacactt acacgcagga aacctctctg aactgggtaa tttaaacaat atgaaccgag    2220
acttagcttt ccatttgttg agagaagtct ctgattattt tcgccagagc gaaccgcata    2280
gcccaatttc atttttgtta gaaaaagcga ttcgatgggg atatttatcc ttacctgagt    2340
tgctgcgaga aatgatgtcg gaacaaaacg tgacgctct tagtacgatt tttaatgccg    2400
ccggattgaa tcatctcgat caggttttgc tgccggaggt gagtactcca acggtgggca    2460
ttgaaagccc ccaaacacct caagcgaagc cttccgtttc ggatccgcga agtgttgaag    2520
agcatgtatc tcagacttcc cctgtagata cccaatctaa gcaagatcaa aaaccacaat    2580
catccgctac gtcggctctg agttggtaat tgtgttaaa aaataaggaa aaatcatggc    2640
aagtatttac atgcgtgtaa gcggtcttca agttgagggc gcagcgacta tcggtcagct    2700
agaaacggct gaaggtaaaa atgacggttg gtttgcaatc aactcttact cttggggtgg    2760
cgctcgtaac gttgctatgg acatcggtaa cggcaccaat gcggattcag gcatggttgg    2820
cgtaagcgaa gttagcgtaa ctaaagaagt cgatggtgct tctgaagacc tactgtctta    2880
tttattcaac ccaggtaaag acggtaaaac tgttgaggtt gcatttacta agccttctaa    2940
cgatggtcaa ggtgcagacg tttacttcca agttaagcta gaaaaagcac gtttagtttc    3000
ttacaacgtg agcgggactg acggatctca accgtacgag agcctatctc tttcttacac    3060
ttctatttct cagaagcatc actatgagaa agaaggtggt gaactacaaa gcggtggtgt    3120
tgtgacttac gacctaccga ccgggaaaat gacttctggt aagtaattct ttcattagac    3180
atgccacgtt aattggcatg tctatttcat gaatatctca ttttaggaca ccgttatggc    3240
attgaactca caacataagc gcgttagtaa gaaccgtgtc agcatcacct atgacgttga    3300
aacgaatggc gccgtaaaga cgaaagagct gccgtttgtt gttggcgtca ttggcgactt    3360
```

-continued

```
ttcaggacac aaaccagaat cagaaaaagt tgatttagaa gagcgagagt tcacgggtat    3420
cgataaagac aacttcgata cagtgatggg gcaaattcac ccgcgtcttt cgtacaaggt    3480
tgataacaag cttgctaatg atgatagcca gtttgaagtg aacttgagcc tccgttcgat    3540
gaaagatttc cacccagaga acttagttga tnaaattgag ccgcttaa                3588
```

<210> SEQ ID NO 2
<211> LENGTH: 463
<212> TYPE: PRT
<213> ORGANISM: Vibrio anguillarum

<400> SEQUENCE: 2

```
Met Pro Leu Ser Lys His Gln Ile Glu Gln Leu Ser Lys Pro Leu Ser
  1               5                  10                  15

Asp Asp Ser Ile Cys Gly Val Tyr Leu Lys Leu Glu Lys Ser Ala Phe
             20                  25                  30

Arg Pro Leu Arg Asn Glu Phe Asn Val Ala Gln Thr Ala Leu Arg Lys
         35                  40                  45

Leu Ser Gln Asn Pro Ser Ala Asp Glu Arg Asp Ala Leu Gln Glu Ala
     50                  55                  60

Cys Leu Asn Lys Trp Lys Ile Leu Ser Asp Ser Leu Tyr Glu Gln Phe
 65                  70                  75                  80

Ser Lys Thr Thr Arg Asp Ile Glu Leu Ile Ser Trp Phe Val Ala Ala
                 85                  90                  95

Gln Phe Leu Leu Asp Thr Thr Leu Glu Ser Ala Ala Asn Ser Leu Glu
            100                 105                 110

Trp Leu Ala Asp Leu Ser Glu Lys His Trp Asp His Leu Asn Pro Val
        115                 120                 125

Leu Pro Val Glu Thr Leu Lys Ser Asp Asp Lys Gly Lys Glu Arg
    130                 135                 140

Glu Gln Ala Asp Ala Lys Val Lys Ala Phe Phe Gln Leu Val Gly Asp
145                 150                 155                 160

Ser Glu Glu Ser Ser Ile Leu Tyr Ala Pro Val Leu Gln Leu Pro Leu
                165                 170                 175

Val Gly Glu Val Thr Phe Phe Asp Phe Gln Ser Ala Glu Arg Lys Gly
            180                 185                 190

Glu Ile Ser Gln Leu Lys Ser Met Leu Thr Thr Val Ala Gln Glu
        195                 200                 205

Arg Phe Ala Ile Gln Phe Lys Met Glu Asn Ala Lys Arg Cys Val Thr
    210                 215                 220

Gln Leu Asp Arg Leu Ser Ala Leu Val Ser Thr Lys Cys His Ser Leu
225                 230                 235                 240

Gly Ser Gln Ser Thr Asn Phe Gly Phe Ala Lys Ser Leu Leu Thr Arg
                245                 250                 255

Val Glu Asn Ala Leu Val His Leu Ser Gly Ile Lys Leu Ala Pro Lys
            260                 265                 270

Ala Glu Ala Lys Thr Val Glu Gln Val Ala Glu Ser Ser Val Ser
        275                 280                 285

Glu Gly Glu Leu Pro Ser His Met Asp Thr Lys His Ile Glu Arg Ile
    290                 295                 300

Pro Met Ala Ser Glu Gln Ala Gln Thr Val Ser Gln His Leu His Ala
305                 310                 315                 320

Gly Asn Leu Ser Glu Leu Gly Asn Leu Asn Asn Met Asn Arg Asp Leu
                325                 330                 335
```

```
Ala Phe His Leu Leu Arg Glu Val Ser Asp Tyr Phe Arg Gln Ser Glu
            340                 345                 350

Pro His Ser Pro Ile Ser Phe Leu Leu Glu Lys Ala Ile Arg Trp Gly
            355                 360                 365

Tyr Leu Ser Leu Pro Glu Leu Leu Arg Glu Met Met Ser Glu Gln Asn
            370                 375                 380

Gly Asp Ala Leu Ser Thr Ile Phe Asn Ala Ala Gly Leu Asn His Leu
385                 390                 395                 400

Asp Gln Val Leu Leu Pro Val Ser Thr Pro Thr Val Gly Ile Glu
            405                 410                 415

Ser Pro Gln Thr Pro Gln Ala Lys Pro Ser Val Ser Asp Pro Arg Ser
            420                 425                 430

Val Glu Glu His Val Ser Gln Thr Ser Pro Val Asp Thr Gln Ser Lys
            435                 440                 445

Gln Asp Gln Lys Pro Gln Ser Ser Ala Thr Ser Ala Leu Ser Trp
            450                 455                 460

<210> SEQ ID NO 3
<211> LENGTH: 176
<212> TYPE: PRT
<213> ORGANISM: Vibrio anguillarum

<400> SEQUENCE: 3

Met Ala Ser Ile Tyr Met Arg Val Ser Gly Leu Gln Val Glu Gly Ala
1               5                   10                  15

Ala Thr Ile Gly Gln Leu Glu Thr Ala Glu Gly Lys Asn Asp Gly Trp
            20                  25                  30

Phe Ala Ile Asn Ser Tyr Ser Trp Gly Gly Ala Arg Asn Val Ala Met
            35                  40                  45

Asp Ile Gly Asn Gly Thr Asn Ala Asp Ser Gly Met Val Gly Val Ser
    50                  55                  60

Glu Val Ser Val Thr Lys Glu Val Asp Gly Ala Ser Glu Asp Leu Leu
65                  70                  75                  80

Ser Tyr Leu Phe Asn Pro Gly Lys Asp Gly Lys Thr Val Glu Val Ala
            85                  90                  95

Phe Thr Lys Pro Ser Asn Asp Gly Gln Gly Ala Asp Val Tyr Phe Gln
            100                 105                 110

Val Lys Leu Glu Lys Ala Arg Leu Val Ser Tyr Asn Val Ser Gly Thr
            115                 120                 125

Asp Gly Ser Gln Pro Tyr Glu Ser Leu Ser Leu Ser Tyr Thr Ser Ile
            130                 135                 140

Ser Gln Lys His His Tyr Glu Lys Glu Gly Glu Leu Gln Ser Gly
145                 150                 155                 160

Gly Val Val Thr Tyr Asp Leu Pro Thr Gly Lys Met Thr Ser Gly Lys
                165                 170                 175

<210> SEQ ID NO 4
<211> LENGTH: 117
<212> TYPE: PRT
<213> ORGANISM: Vibrio anguillarum
<220> FEATURE:
<221> NAME/KEY: MOD_RES
<222> LOCATION: (113)
<223> OTHER INFORMATION: Variable amino acid

<400> SEQUENCE: 4

Met Ala Leu Asn Ser Gln His Lys Arg Val Ser Lys Asn Arg Val Ser
1               5                   10                  15
```

-continued

```
Ile Thr Tyr Asp Val Glu Thr Asn Gly Ala Val Lys Thr Lys Glu Leu
            20                  25                  30

Pro Phe Val Val Gly Val Ile Gly Asp Phe Ser Gly His Lys Pro Glu
            35                  40                  45

Ser Glu Lys Val Asp Leu Glu Glu Arg Glu Phe Thr Gly Ile Asp Lys
    50                  55                  60

Asp Asn Phe Asp Thr Val Met Gly Gln Ile His Pro Arg Leu Ser Tyr
65              70                  75                      80

Lys Val Asp Asn Lys Leu Ala Asn Asp Asp Ser Gln Phe Glu Val Asn
            85                  90                  95

Leu Ser Leu Arg Ser Met Lys Asp Phe His Pro Glu Asn Leu Val Asp
            100                 105                 110

Xaa Ile Glu Pro Leu
    115
```